(12) United States Patent
Fischer et al.

(10) Patent No.: US 8,100,958 B2
(45) Date of Patent: Jan. 24, 2012

(54) DEVICE FOR DELIVERING A SELF-EXPANDING STENT IN A VESSEL OF THE BODY

(75) Inventors: Heike Fischer, Meerbusch (DE); Marcos Centola, Sao Paulo (BR)

(73) Assignee: JOTEC GmbH, Hechingen (DE)

( * ) Notice: Subject to any disclaimer, the term of this patent is extended or adjusted under 35 U.S.C. 154(b) by 400 days.

(21) Appl. No.: 12/070,537

(22) Filed: Feb. 19, 2008

(65) Prior Publication Data
US 2008/0208209 A1  Aug. 28, 2008

(30) Foreign Application Priority Data
Feb. 22, 2007  (DE) .......................... 10 2007 010 305

(51) Int. Cl.
*A61F 2/06* (2006.01)
(52) U.S. Cl. ...................................... 623/1.11
(58) Field of Classification Search ................ 623/1.11, 623/1.2; 606/108, 194
See application file for complete search history.

(56) References Cited

U.S. PATENT DOCUMENTS

| | | | |
|---|---|---|---|
| 4,411,653 A | 10/1983 | Razi | |
| 4,444,560 A | 4/1984 | Jacklich | |
| 4,820,287 A | 4/1989 | Leonard | |
| 5,026,377 A | 6/1991 | Burton et al. | |
| 5,707,376 A | 1/1998 | Kavteladze et al. | |
| 5,944,727 A * | 8/1999 | Ahari et al. | 606/108 |
| 5,994,727 A * | 11/1999 | Lee | 257/280 |
| 6,136,006 A | 10/2000 | Johnson et al. | |
| 6,402,760 B1 | 6/2002 | Fedida | |
| 6,514,261 B1 * | 2/2003 | Randall et al. | 606/108 |
| 7,105,016 B2 * | 9/2006 | Shiu et al. | 623/1.12 |
| 2002/0004676 A1 * | 1/2002 | Wallace et al. | 623/1.12 |
| 2003/0191516 A1 | 10/2003 | Weldon et al. | |
| 2004/0138734 A1 | 7/2004 | Chobotov et al. | |

(Continued)

FOREIGN PATENT DOCUMENTS

DE 69806550 11/2002
(Continued)

OTHER PUBLICATIONS

European Search Report for European Patent Application No. EP09169903 dated Dec. 23, 2009.

*Primary Examiner* — Kathleen Sonnett
*Assistant Examiner* — Jocelin Tanner
(74) *Attorney, Agent, or Firm* — Knobbe Martens Olson & Bear, LLP

(57) ABSTRACT

The present invention relates to a device for delivering a self-expanding stent in a vessel of the body. The device comprises a tubular sheath which, in a distal section, keeps the stent radially compressed, and a pusher element, which is guided in the tubular sheath, in order to stabilize the stent when the sheath is pulled back. A handle is also provided, with a passage via which the pusher element is secured on the handle. The device further comprises a tubular rod which is fixedly connected to the handle and inside which the pusher element is provided, and which is provided at least in part with regularly spaced elevations and with depressions lying between the elevations. In addition, a movable element is provided which is arranged movably over the rod, distally from the handle, and whose movement in the proximal direction allows the sheath to be pulled back.

7 Claims, 1 Drawing Sheet

U.S. PATENT DOCUMENTS

| | | |
|---|---|---|
| 2004/0176682 A1 | 9/2004 | Murphy |
| 2005/0149159 A1* | 7/2005 | Andreas et al. .............. 623/1.11 |
| 2006/0184238 A1 | 8/2006 | Kaufmann et al. |
| 2006/0224227 A1* | 10/2006 | Chobotov .................... 623/1.12 |
| 2008/0188920 A1* | 8/2008 | Moberg et al. ............... 623/1.12 |

FOREIGN PATENT DOCUMENTS

| | | |
|---|---|---|
| DE | 10335649 | 2/2005 |
| DE | 102004023559 | 9/2005 |
| DE | 102005059261 | 6/2007 |
| EP | 1 078 611 A1 | 2/2001 |
| EP | 1 210 959 | 6/2002 |
| EP | 1391181 | 2/2004 |
| EP | 1415616 | 5/2004 |
| EP | 1 440 671 | 7/2004 |
| EP | 1440672 | 7/2004 |
| EP | 1 117 341 B1 | 12/2004 |
| EP | 1894545 | 3/2008 |
| EP | 1923024 | 5/2008 |
| EP | 1943988 | 7/2008 |
| JP | 58-086175 A | 5/1983 |
| JP | 62-243552 A | 10/1987 |
| JP | 10-511016 A | 10/1998 |
| WO | WO 96/00261 | 5/1995 |
| WO | WO 00/18330 | 4/2000 |
| WO | WO2005/067819 A1 | 7/2005 |

* cited by examiner

DEVICE FOR DELIVERING A SELF-EXPANDING STENT IN A VESSEL OF THE BODY

CROSS-REFERENCES TO RELATED APPLICATIONS

This application claims priority from German patent application DE 10 2007 010 305.2, filed on Feb. 22, 2007.

BACKGROUND OF THE INVENTION

The present invention relates to a device for delivering a self-expanding stent into a vessel of the body, with a tubular sheath which, in a distal section, keeps the stent radially compressed, a pusher element which is guided in the tubular sheath, in order to stabilize the stent when the sheath is pulled back, and a handle that has a passage via which the pusher element is secured on the grip.

Insertion systems of this kind and stents are generally known from the prior art.

Such insertion systems are used to implant endovascular stents into blood vessels that have been damaged, for example as a result of diseases or the like, or that have been widened by an aneurysm or have had their lumen occluded, as a consequence of which the function of the vessels is greatly impaired or there is a risk of the vessels rupturing. In the prior art, various implantable stent devices are known which, after they have been implanted, keep blood vessels, for example arteries, open or delimit aneurysms from the blood stream. Such stents generally have a tubular body which is inserted into the vessel and is fixed at the relevant location in order to keep the lumen of the vessel open.

Thus, the prior art includes stent grafts, for example, which have a wire framework made of a self-expanding material, and the wire framework can additionally be connected with a tube made of textile or PTFE.

For implantation, the stent or stent graft is radially compressed, such that its cross-sectional surface area can be considerably reduced and it can easily be inserted into the vessel. On account of the resiliency of the metal framework or metal stent, the stent expands back to its original shape and in so doing stretches its jacket surface, which wedges itself internally in the blood vessel.

For implantation, the stents are folded up radially and, with the aid of catheters advanced through the lumen, are then introduced into the blood vessel and placed in the correct position in the vessel. The correct position of the stent can be monitored using X-ray markers, for example. To ensure that the stents remain in the folded-up state during their positioning, they are arranged in a sheath or in a sheath-like tube, which presses the stent radially inwards and compresses it. This so-called withdrawal sheath is pulled back after the stent has been positioned in the vessel, in which process the stent is held axially by an abutment element/slide element, which is also designated as a pusher. The pusher lies in contact with the stent and holds the latter in its axial position, while the withdrawal sheath also surrounding the pusher is detached from the stent, which is thus able to expand and wedge itself in the blood vessel.

When releasing a self-expanding stent or stent graft, the physician often has to apply a considerable force to the pulling grip of the tubular sheath and to the grip used for positioning the implant and connected to the pusher.

The force applied is necessitated, on the one hand, by friction between the outer wall of the stent/stent graft, strongly compressed counter to its expansion forces, and the inner wall of the tubular sheath, and, on the other hand, also by frictional forces between the movable parts of the insertion system and deflecting force components caused by anatomical windings of the access vessel and aorta.

Moreover, the operating physician has to bear in mind that, when removing the sleeve, the stent ought not to be able to shift from the location at which it is specifically intended to be placed.

The considerable force applied when releasing an aortic stent graft places a physical strain on the physician and can lead to an abrupt release of the stent/stent graft on transition from static friction to kinetic friction in the insertion system. In this situation, it is very difficult for the physician to compensate the abrupt release movements on the insertion system such that he can precisely maintain the position of the stent graft with the pusher and at the same time avoid a slipping movement and resulting damage to the vessel wall.

EP 1 117 341 A discloses a delivery system for implantable stents, said system comprising a stabilizing element with a tubular spring, which extends through the catheter between the outer jacket and the inner tube in order to maintain the position of the stent when the outer jacket (pusher) is pulled back. The system disclosed in EP 1 117 341 A also comprises a grip which is designed as an elongate housing with a passage, and a movable element which is guided in the housing and has a pawl hub, one side of which is in engagement with a stationary ratchet, and the other side of which is in engagement with a movable ratchet. The movable ratchet is in engagement with a pinion, and the latter is in turn in engagement with a drive wheel, which is located on the housing. All the elements—stationary ratchet, movable ratchet and movable element—are guided in the housing. The device is actuated manually via a lever provided on the grip.

The prior art also includes delivery systems with what are known as pistol grips, but these are not very ergonomic, and the awkward operation of the system during release of the stent graft can lead to a clenched hold on the part of the user.

SUMMARY OF THE INVENTION

Against this background, an object of the present invention is to make available an alternative delivery system which can be operated easily and without applying excessive force, and which permits a uniform, step-by-step release of stents/stent grafts.

According to one aspect of the invention, there is provided a device for delivering a self-expanding stent into a vessel of the body, with a tubular sheath which, in a distal section, keeps the stent radially compressed, a pusher element which is guided in the tubular sheath, in order to stabilize the stent when the sheath is pulled back, and a handle that has a passage via which the pusher element is secured on the grip, said device further comprising a tubular rod which is fixedly connected at least to the handle and inside which the pusher element is provided, and which is provided at least in part with regularly spaced elevations and with depressions lying between the elevations, and said device further comprising a movable element which is arranged so as to be movable over the rod, distally from the handle, and whose movement in the proximal direction allows the tubular sheath to be pulled back.

The pusher element (or the "pusher") in the device according to the invention is fixedly connected to the handle and the tubular rod. In this way, both the axial and also the rotational position of the stent/stent graft can be controlled by the proximal handle.

With the disclosed insertion system, it is now possible to pull the sheath back slowly and step by step, without running any risk of this movement converting into an abrupt mechanism. The movable element also affords the possibility of pulling the tubular sheath back with minimal force from the stent/stent graft that is to be released. Alternatively, the insertion system can be taken hold of at the handle and at the movable element, and the movable element can be moved along the rod uniformly in the direction of the handle, such that the withdrawal sheath slides smoothly over the stent, which is in turn held at the desired position by the pusher element. This is achieved by the operating physician for example holding the insertion system at the grip with one hand, while the other hand moves the movable element along the rod towards the user, i.e. in the proximal direction. The sheath is carried along by this movement and releases the stent, which is compressed by the sheath. In this way, the stent is able to expand and bear, for example, on the vessel walls.

As has just been explained, "proximal direction" signifies the direction leading towards the user. In a development of the device according to the invention, a securing means can be provided on the movable element to prevent the movable element from slipping in the distal direction, i.e. away from the user, and thus to prevent slipping of the stent and to prevent damage to the vessel wall.

According to a refinement, it is preferred if the movable element has an actuating means by which the movable element can be moved step by step in relation to the rod.

This embodiment has the advantage that the sheath can be released in a controlled manner, i.e. step by step, thereby advantageously avoiding uncontrolled and excessively rapid movements that could cause the positioned stent to slip out of place.

It is preferred in particular if the actuating means comprises a lever grip and at least one thrust element or push element which is connected via a first end to the lever grip in such a way the force exerted by a movement of the lever grip is transmitted to the thrust element. The thrust element additionally comprises a second end which engages in the depressions between the elevations of the rod and which is designed in such a way that a movement of the movable element in the distal direction is blocked.

This feature has the advantage that the movable element can be moved by a simple pressing movement on the lever grip that is coupled to it. This lever movement is transmitted to the thrust element, which is connected with one of its ends to the lever grip. The other end of the thrust element engages in a depression of the rod and transmits this movement and the force in the axial direction, that is to say along the rod and to the movable element. By the movement of the movable element, the tubular sheath coupled with a force fit to the movable element is also pulled simultaneously in the proximal direction. In this way, the tubular sheath is pulled along the stent held in position by the pusher element, as a result of which the stent is released. After the lever grip is let go, the thrust element engages in the next unit of the rod, as a result of which the movable element is displaced again in the proximal direction.

The thrust element can be connected to the lever arm in an articulated manner via its first end, for example.

By repeated actuation and release of the lever grip, the stent can advantageously be released step by step at the desired position in the vessel, without having to apply strong forces and without the risk of abrupt movements that could possibly cause the stent to slip out of position.

With the device according to the invention, the pressure force is strengthened by a multiple via the transmitted lever action.

This device is therefore particularly suitable for the insertion of quite long stents of large diameter, for example aortic stents and abdominal stents. Moreover, high release forces occasioned by highly tortuous and calcified vessel access routes can be overcome.

In the device according to the invention, it is preferred if the lever grip has a shape adapted to the outer shapes of the movable element.

This embodiment has the advantage that the lever grip can be completely pressed together with the movable element, such that the lever grip lodges in a recess of the movable element and, in this way, the position of excursion of the lever grip in one direction is limited.

It is also preferred if a spring is provided, which pretensions the lever grip into an opened position.

This has the advantage that the lever grip of the movable element flips away from the grip by the spring action; by repeated actuation of or pressure on the lever grip counter to the spring force in the direction of the movable element, the mechanism described above is set in motion. To release the stent/stent graft, the lever grip is thus pressed counter to the spring force in the direction of the movable element, as a result of which the thrust element, which is connected to the lever grip, can engage and catch in the regularly spaced depressions of the rod. By repeated actuation of the lever grip, the movable element is then pulled back step by step, as a result of which the tubular sheath is pulled along with it and the stent is released. The force transmission in the axial direction thus takes place when the lever grip is pressed down. During the upward movement, the thrust element engages and catches in the next depression.

The spring can be provided for example between the movable element and the lever grip.

In a refinement it is also preferred if the movable element comprises a catch element which is designed engaging with the depressions between the elevations of the rod in such a way that a movement of the movable element is blocked in the distal direction and is allowed in the proximal direction.

In a development of the device according to the invention, it is preferred if a carrier is also provided, which is mounted axially movably in the tubular rod and is connected to the movable element in the axial direction with a force fit, and via which carrier the tubular sheath is coupled to the movable element.

This embodiment has the advantage that, upon an axial movement of the movable element, the carrier, which is coupled to the movable element and to which the sheath is in turn coupled, is also moved along too. The stent can thus be pulled back by transmission of the movement to the carrier from the stent, as a result of which the latter is released. The carrier can run in a groove of the tubular rod, as a result of which this element is easier to guide. The carrier and the movable element are connected with a force fit in the axial direction and form one unit. However, the movable element can be rotated independently of the carrier and can thus be turned to a position favourable to the user. This also ensures that the orientation of a non-rotationally symmetrical stent is not changed by a rotation of the movable element.

In another embodiment, it is preferred if the insertion system has triggers whose actuation allows the movable element to be moved freely in the proximal direction.

This has the advantage that the movable element can be pulled in the direction of the user, i.e. in the proximal direction, in one go, avoiding the individual steps defined by the rod. This is desirable especially when the stent is safely positioned and has already been at least partially released. To accelerate the complete release, the triggers can then be actuated, which release the at least one thrust element and have the effect that the thrust element can no longer engage in the depressions of the rod.

In another embodiment, it is preferred if the distance between the regularly spaced elevations of the rod is such that the thrust element engages in the bottom of the next distal depression between the elevations after the lever grip has sprung back from the movable element.

This embodiment ensures that a careful, step-by-step movement of the movable element, and thus of the tube, a corresponding release of the stent can be effected. The length of the distance travelled between one elevation and the next one can vary depending on the design of the rod and the desired use. Thus, for example, a travel of ca. 1 mm to 8 mm, in particular of 4 mm, can be obtained. However, this is a variable parameter that can be adapted by changing the spacing and/or width of the elevations to the particular use and purpose.

In another embodiment, it is preferred if the rod with the elevations is designed as a toothed rod with teeth, that is to say, as a toothed rack.

This embodiment has the advantage that the thrust element can engage with its second end in the teeth, being pressed by a spring force into the bottom of the tooth. The shape and size of the teeth may vary. However, it is preferred if the surface of the teeth on which the thrust element transmits the force has a perpendicular surface, and the other surface of the teeth has an oblique surface. In this way, the engagement and latching of the thrust element is optimally assisted.

Suitable materials that can be used for producing the insertion system according to the invention for a stent are—for the grip parts and the movable element or carrier—reinforced and non-reinforced thermoplastics such as polycarbonate (PO), polyoxymethylene (POM), polyester (PET), polypropylene (PP), polyamide (PA), polyethylene (PE), polyvinyl chloride (PVC) or mixtures thereof. Moreover, parts of the insertion system can be made of steel or non-ferrous alloys (for example titanium alloys).

Further advantages and features will become evident from the following description and the attached figures.

It is self-evident that the aforementioned features and the features still to be explained below can be used not only in the respectively cited combination but also in other combinations or singly, without departing from the scope of the present invention.

BRIEF DESCRIPTION OF THE DRAWING

An illustrative embodiment of the invention is depicted in the attached FIGURE and is described in more detail below with reference to said FIGURE.

DESCRIPTION OF PREFERRED EMBODIMENTS

Figure 1:
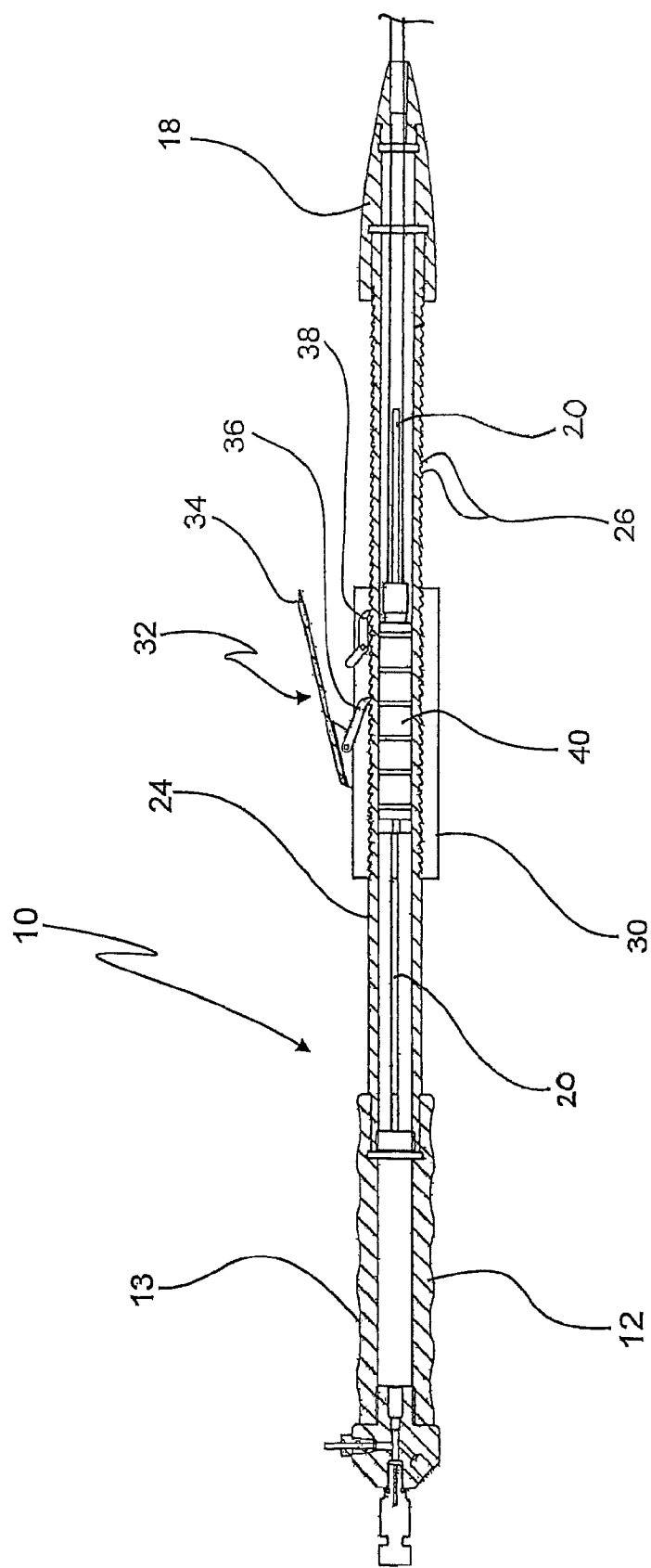
FIG. 1 shows a schematic cutaway view of a first illustrative embodiment of the device according to the invention for inserting a self-expanding stent into a vessel.
Figure 1:
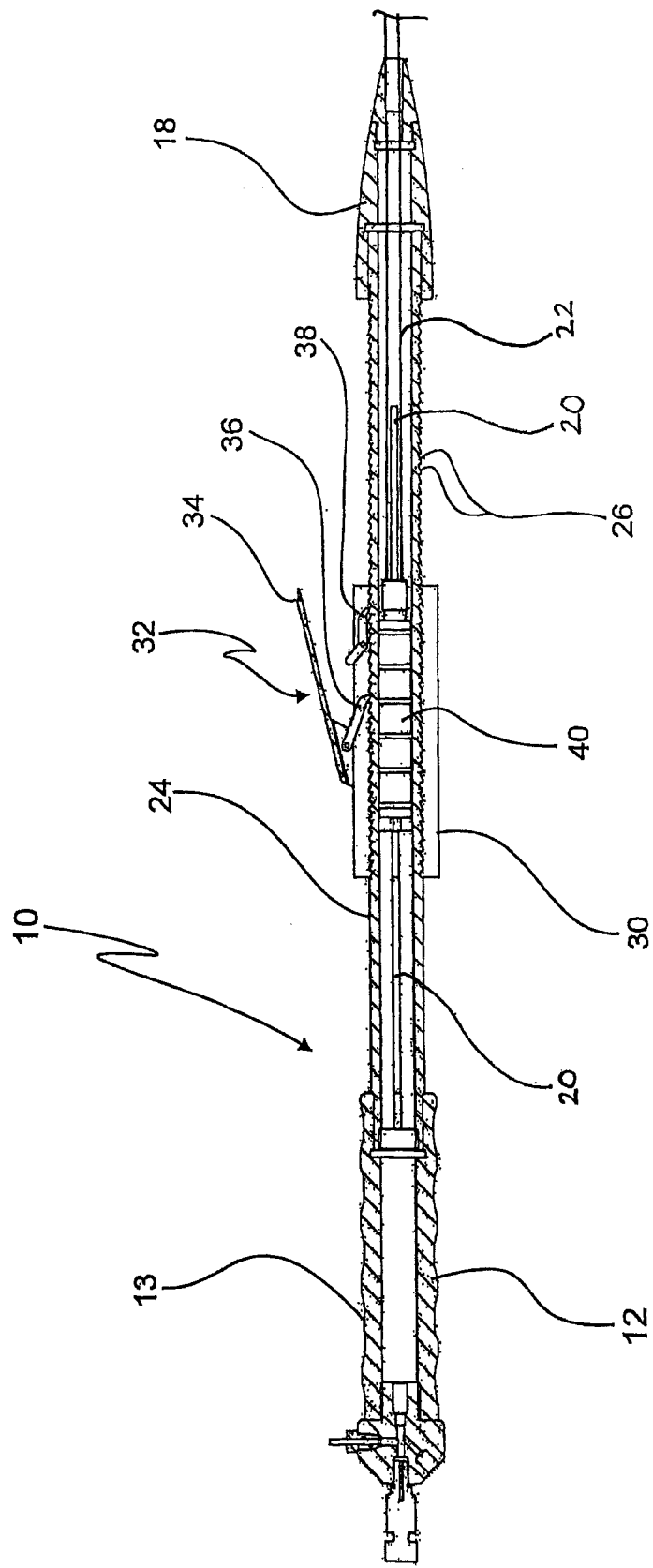

The device according to the invention is shown partially in cross section in FIG. 1 and greatly shortened and not true to scale.

A device for inserting a stent is shown in cutaway view in FIG. 1, where elements that are customary in stent insertion systems have been omitted for the sake of clarity. The device includes a tubular sheath 22 that keeps the stent radially compressed for insertion into a vessel. The loaded stent/stent graft is also not shown, nor the wire guide catheter, the soft silicone tip, and a possible attachment for the stent springs at the proximal end of the stent. A guide wire, which is also not shown, can be guided through the wire guide catheter.

In FIG. 1, a grip system of a device according to the invention is designated overall by reference number 10. It comprises a handle 12 and a rod 24. The handle 12 can have an outer shape adapted to the hand or the fingers of a user, i.e. shallow depressions 13 adapted to the fingers and providing a better purchase on the handle 12.

At the distal end, the device further comprises a cap 18, but the latter is not inserted into the vessel. The cap 18 is provided for guiding the tubes and optionally for holding together the rod, which can be assembled from two half shells. The device further comprises a pusher element (pusher) 20, which is shown only in section in FIG. 1 and, in the insertion system true to scale, is much longer than the handle 12. For insertion of the stent, the pusher element 20 is located between tubular sheath 22 and wire guide catheter in the form of a tube.

The grip 12 is fixedly connected to an end cap 42, which serves as a receiving element or passage for the pusher element, or pusher, the wire guide catheter (not shown), optionally a support tube (not shown), an irrigation tube (not shown) and the trigger mechanism of a spring fixture (not shown). A support tube can be fitted inside the handle system, in order to increase the stability of the pusher element (pusher) upon axial loading. For this purpose, the support tube can be located inside or outside of the pusher and should bear as tightly as possible on the pusher.

The rod 24 is provided in part (in the distal area in FIG. 1) with regularly spaced elevations 26. The rod 24 is coupled directly to the handle 12. Depressions are formed between the regularly spaced elevations. The rod 24 is designed in FIG. 1 as a toothed rack with teeth 26, which have an oblique surface pointing in the proximal direction and thus present an asymmetric tooth profile in the axial direction.

Reference number 30 in FIG. 1 designates the movable element, which is arranged to be movable along the rod 24 connected to the handle 12, that is to say is arranged to be displaceable in the distal direction and rotatable on the toothed rod. An actuating means, designated overall by reference number 32 in FIG. 1, is provided on the movable element 30. The movable element 30 can be moved in a controlled manner via the actuating means. In FIG. 1, the actuating means comprises a lever grip 34 and at least one thrust element 36 which at a first end is connected to the lever grip 34 in an articulated manner and at its second end is designed to engage in the depressions of the rod 24. By means of a spring (not shown in FIG. 1), the lever grip 34 is pretensioned away from the movable element 30, such that the lever grip 34 in the unloaded position is forced away from the movable element. By pressing and loading the lever grip 34 in the direction of the movable element 30, the thrust element 36 is also moved.

It will be seen from FIG. 1 that, upon actuation of the lever grip 34, this movement is transmitted to the thrust element 36, as a result of which the movable part 30 is pushed in the proximal direction, that is to say in the direction of the handle 12. During this movement, a catch element 38 springs into the next proximal depression of the rod 24. The catch element 38 is designed such that it engages in the depression between the elevations of the rod 24. By means of this catch element 38, the movement of the movable element 30 is blocked in the distal direction and is freed in the proximal direction.

The insertion system in FIG. 1 also comprises a carrier 40, which is coupled to the movable element 30 and runs in a groove of the rod 24, which groove is not shown in FIG. 1. The tubular sheath is clamped in the carrier 40 and is moved in the proximal direction by the movement of the movable element 30 and of the carrier 40 coupled thereto, as a result of which the stent is released and is able to expand.

The person using the insertion system thus places one hand round the handle 12 and the other hand round the actuating means 32. The latter can be actuated by repeated pressing of the lever grip 34. Each time it is let go, the lever grip 34 always flaps back away from the movable element 30 on account of the action of the compression spring.

As has already been mentioned above, a wire guide catheter with an atraumatic tip is also provided for inserting the stent into a vessel, said catheter being guided by the pusher element (pusher) also surrounded by the tube 14. The pusher keeps the stent in position upon its release and counteracts the tensile force acting in the proximal direction upon release of the stent.

Referring to FIG. 1, we will now describe the mechanism by which, with each pressing down on the lever grip 34, the sleeve tube is pulled back step by step and releases the stent.

In the embodiment shown in FIG. 1, the lever grip 34 can be pressed down in two stages. The first stage corresponds to the pressing-down action until contact with the catch element and serves for pulling the tubular sheath back step by step. When the lever grip is pressed down further, which corresponds to stage two, the thrust element 36 and the catch element 38 are lifted from the teeth 26 of the rod 24, and the movable element can be moved freely to and fro on the rod 24.

The stent loaded into the insertion system is introduced in compressed form into the desired vessel. A locking button can be provided, for example, which first has to be unlocked after insertion, and before the start of the stent release, and which is intended to prevent the lever grip from being accidentally actuated too early. For this purpose, the locking button can be secured displaceably in a groove of the lever grip. A relative movement between tube and slide element/pusher is therefore not possible.

The lever 34 then flips away from the movable element 30 on account of the action of the compression spring, for example by undoing the locking button. The thrust element 36 and the catch element 38 then press into the depressions of the rod 24. The rod 24 is fixedly connected to the handle 12. The flank angles of the catch element 38 and of the rod 24 are such that a movement of the sleeve tube in the distal direction is blocked by the catch element 38. The thrust element 36 is connected to the lever grip 34 via a pivot hinge. The movement of the movable element transmits itself to the movement of the sleeve tube, such that the latter is pulled in the proximal direction and the stent is released.

To be able to release the stent/stent graft more quickly, or to be able to close the insertion system again after implantation of the stent, it is possible, in the second stage of the lever grip 34 in another embodiment, to actuate a trigger provided on the movable element and thus release the movable element 30 from the step-by-step actuating mechanism and guide it in one go in the proximal or distal direction.

The spacing between the teeth on the rod 24 can be dimensioned such that, after the lever grip 34 has been let go and flips back from the movable element 30, the thrust element 36 catches in the next proximal gap between teeth. It will be appreciated that the rod does not necessarily have to be provided with teeth, and other designs with elevations and depressions are also conceivable.

With each actuation of the lever grip 34, the sleeve tube is thus pulled back by the distance of a tooth spacing.

With the movable element 30 and the rod 24 connected fixedly to the handle 12, the person using the device can in this way comfortably control the axial rotation-related position of the stent/stent graft and control the complete or partial release. Moreover, by actuating the trigger, the user can at any time pull back or advance the sleeve tube in a conventional manner in one go.

Advantageously, the system according to the invention can be used not only to release stents and stent grafts, but also in intraluminal heart valves.

Therefore, what is claimed is:

1. A device for releasing a self-expanding stent in a vessel of the body, comprising:
   a tubular sheath which, in a distal section, keeps the stent radially compressed,
   a pusher element which is guided in the tubular sheath, in order to stabilize the stent when the tubular sheath is pulled back,
   a handle, with a passage via which the pusher element is secured on a grip,
   a tubular rod which is fixedly connected to the handle and inside which the pusher element is provided, and which is provided at least in part with regularly spaced elevations and with depressions lying between the elevations;
   a movable element which is arranged movably over the rod, distally from the handle, and whose movement in a proximal direction allows the tubular sheath to be pulled back, wherein the movable element has an actuating means by which the movable element can be moved step by step in relation to the rod, and wherein the actuating means comprises a lever grip and at least one thrust element which is connected via a first end to the lever grip and which at its second end is designed to engage in the depressions between the elevations of the rod in such a way that a movement of the movable element in the distal direction is blocked; and
   a carrier coupled to the movable element, said carrier being mounted axially movably within the tubular rod and connected to the movable element in the axial direction with a force fit, wherein the tubular sheath is coupled to the movable element via said carrier.

2. The device of claim 1, wherein a spring is provided, the spring adapted to pretension the lever grip away from the movable element.

3. The device of claim 1, wherein the actuating means comprises at least one catch element which is designed engaging with the depressions between the elevations of the rod in such a way that a movement of the movable element in the distal direction is blocked by the catch element and is freed in the proximal direction.

4. The device of claim 1, wherein the rod has a groove for receiving the carrier movably in the groove.

5. The device of claim 1, wherein at least one trigger is provided that permits the free movement of the movable element in the proximal or distal direction.

6. The device of claim 1, wherein the distance between the elevations of the rod is such that the thrust element engages in the next proximal depression after the lever grip has sprung back from the movable element.

7. The device of claim 1, wherein the pusher element is fixedly connected to the handle and the tubular rod.

* * * * *

UNITED STATES PATENT AND TRADEMARK OFFICE
CERTIFICATE OF CORRECTION

PATENT NO. : 8,100,958 B2
APPLICATION NO. : 12/070537
DATED : January 24, 2012
INVENTOR(S) : Heike Fischer et al.

It is certified that error appears in the above-identified patent and that said Letters Patent is hereby corrected as shown below:

The Title page, showing an illustrative Figure, should be deleted and substitute therefor the attached title page.

Please replace Fig. 1 with the attached drawing, in which reference numeral 22 has been added.

Signed and Sealed this
Ninth Day of April, 2013

Teresa Stanek Rea
*Acting Director of the United States Patent and Trademark Office*

CERTIFICATE OF CORRECTION (continued)

(12) United States Patent
Fischer et al.

(10) Patent No.: US 8,100,958 B2
(45) Date of Patent: Jan. 24, 2012

(54) DEVICE FOR DELIVERING A SELF-EXPANDING STENT IN A VESSEL OF THE BODY

(75) Inventors: Heike Fischer, Meerbusch (DE); Marcos Centola, Sao Paulo (BR)

(73) Assignee: JOTEC GmbH, Hechingen (DE)

(*) Notice: Subject to any disclaimer, the term of this patent is extended or adjusted under 35 U.S.C. 154(b) by 400 days.

(21) Appl. No.: 12/070,537

(22) Filed: Feb. 19, 2008

(65) Prior Publication Data
US 2008/0208209 A1  Aug. 28, 2008

(30) Foreign Application Priority Data
Feb. 22, 2007 (DE) .......... 10 2007 010 305

(51) Int. Cl.
*A61F 2/06* (2006.01)
(52) U.S. Cl. .......... 623/1.11
(58) Field of Classification Search .......... 623/1.11, 623/1.2; 606/108, 194
See application file for complete search history.

(56) References Cited

U.S. PATENT DOCUMENTS

| | | | |
|---|---|---|---|
| 4,411,653 A | 10/1983 | Razi | |
| 4,444,560 A | 4/1984 | Jacklich | |
| 4,820,287 A | 4/1989 | Leonard | |
| 5,026,377 A | 6/1991 | Burton et al. | |
| 5,707,376 A | 1/1998 | Kavteladze et al. | |
| 5,944,727 A * | 8/1999 | Ahari et al. | 606/108 |
| 5,994,727 A * | 11/1999 | Lee | 257/280 |
| 6,136,006 A | 10/2000 | Johnson et al. | |
| 6,402,760 B1 | 6/2002 | Fedida | |
| 6,514,261 B1 * | 2/2003 | Randall et al. | 606/108 |
| 7,105,016 B2 * | 9/2006 | Shiu et al. | 623/1.12 |
| 2002/0004676 A1 * | 1/2002 | Wallace et al. | 623/1.12 |
| 2003/0191516 A1 | 10/2003 | Weldon et al. | |
| 2004/0138734 A1 | 7/2004 | Chobotov et al. | |

(Continued)

FOREIGN PATENT DOCUMENTS
DE  69806550  11/2002
(Continued)

OTHER PUBLICATIONS

European Search Report for European Patent Application No. EP09169903 dated Dec. 23, 2009.

*Primary Examiner* — Kathleen Sonnett
*Assistant Examiner* — Jocelin Tanner
(74) *Attorney, Agent, or Firm* — Knobbe Martens Olson & Bear, LLP

(57) ABSTRACT

The present invention relates to a device for delivering a self-expanding stent in a vessel of the body. The device comprises a tubular sheath which, in a distal section, keeps the stent radially compressed, and a pusher element, which is guided in the tubular sheath, in order to stabilize the stent when the sheath is pulled back. A handle is also provided, with a passage via which the pusher element is secured on the handle. The device further comprises a tubular rod which is fixedly connected to the handle and inside which the pusher element is provided, and which is provided at least in part with regularly spaced elevations and with depressions lying between the elevations. In addition, a movable element is provided which is arranged movably over the rod, distally from the handle, and whose movement in the proximal direction allows the sheath to be pulled back.

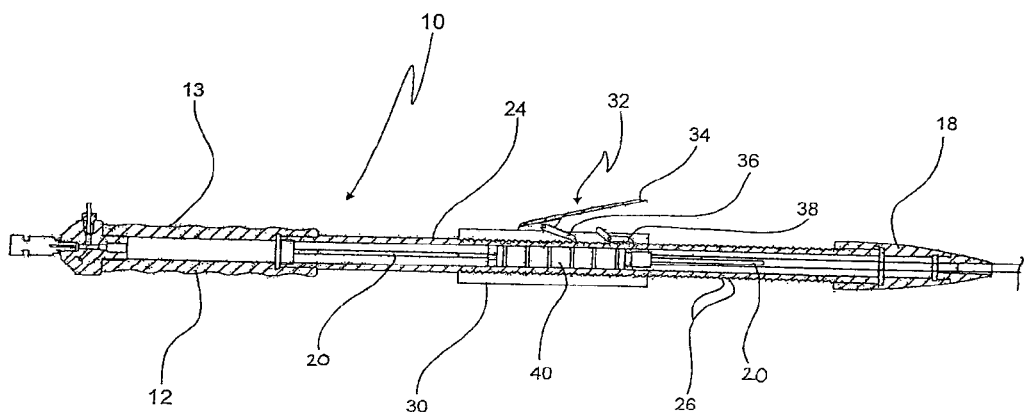

7 Claims, 1 Drawing Sheet